US009460509B2

(12) United States Patent
Funabasama

(10) Patent No.: US 9,460,509 B2
(45) Date of Patent: Oct. 4, 2016

(54) IMAGE PROCESSING APPARATUS, MEDICAL IMAGE DIAGNOSIS APPARATUS, AND IMAGE PROCESSING METHOD

(71) Applicant: Toshiba Medical Systems Corporation, Otawara-shi (JP)

(72) Inventor: Shintaro Funabasama, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/680,201

(22) Filed: Apr. 7, 2015

(65) Prior Publication Data

US 2015/0221089 A1    Aug. 6, 2015

Related U.S. Application Data

(63) Continuation of application No. PCT/JP2013/078742, filed on Oct. 23, 2013.

(30) Foreign Application Priority Data

Oct. 23, 2012    (JP) .................................. 2012-233609

(51) Int. Cl.
  *G06K 9/00*    (2006.01)
  *G06T 7/00*    (2006.01)
  (Continued)

(52) U.S. Cl.
  CPC ........... *G06T 7/0016* (2013.01); *A61B 5/0263* (2013.01); *A61B 5/0275* (2013.01); *A61B 5/02755* (2013.01); *A61B 5/055* (2013.01);
  (Continued)

(58) Field of Classification Search
  None
  See application file for complete search history.

(56) References Cited

U.S. PATENT DOCUMENTS

| 2006/0004279 A1* | 1/2006 | Ikeda ..................... A61B 6/507 600/411 |
| 2007/0112264 A1 | 5/2007 | Wu et al. |

(Continued)

FOREIGN PATENT DOCUMENTS

| JP | 2007-525250 A | 9/2007 |
| JP | 2007-536048 A | 12/2007 |
| JP | 2010-213760 A | 9/2010 |

OTHER PUBLICATIONS

International Search Report mailed Jan. 21, 2014 for PCT/JP2013/078742 filed Oct. 23, 2013 with English Translation.
(Continued)

*Primary Examiner* — Hadi Akhavannik
(74) *Attorney, Agent, or Firm* — Oblon, McClelland, Maier & Neustadt, L.L.P.

(57) ABSTRACT

In an image processing apparatus according to an embodiment, a noise information obtaining unit obtains information about an obstructive factor that is related to the precision level of perfusion images and is contained in pieces of medical image data acquired chronologically; on the basis of a TDC at an inflow blood vessel for an analysis target tissue of which the perfusion state is analyzed and on the basis of a perfusion model of the analysis target tissue, an estimating unit estimates a TDC of the analysis target tissue; on the basis of the estimated TDC of the analysis target tissue and on the basis of the information about the obstructive factor, a generating unit generates assessment information used for assessing reliability of the perfusion images generated from the pieces of medical image data; and a display control unit exercises control so that a display unit displays the assessment information.

12 Claims, 11 Drawing Sheets

(51) Int. Cl.
*A61B 5/055* (2006.01)
*A61B 6/03* (2006.01)
*A61B 6/00* (2006.01)
*G01R 33/56* (2006.01)
*G01R 33/563* (2006.01)
*A61B 5/026* (2006.01)
*A61B 5/0275* (2006.01)

(52) U.S. Cl.
CPC .............. *A61B 6/032* (2013.01); *A61B 6/481* (2013.01); *A61B 6/507* (2013.01); *A61B 6/5205* (2013.01); *G01R 33/5608* (2013.01); *G01R 33/56366* (2013.01); *A61B 6/504* (2013.01); *G06T 2207/10072* (2013.01); *G06T 2207/10081* (2013.01); *G06T 2207/10088* (2013.01); *G06T 2207/30104* (2013.01)

(56) References Cited

U.S. PATENT DOCUMENTS

| 2007/0167731 | A1 | 7/2007 | Taxt et al. | |
| 2009/0028409 | A1* | 1/2009 | Tsukagoshi | A61B 6/032 382/131 |
| 2009/0129536 | A1* | 5/2009 | Ichihara | A61B 6/481 378/4 |
| 2010/0067767 | A1* | 3/2010 | Arakita | A61B 6/507 382/131 |
| 2010/0114064 | A1* | 5/2010 | Kalafut | A61B 5/411 604/508 |
| 2010/0183207 | A1* | 7/2010 | Sakaguchi | A61B 6/507 382/128 |
| 2010/0272344 | A1* | 10/2010 | Ichihara | A61B 6/032 382/132 |
| 2010/0278410 | A1* | 11/2010 | Ohishi | A61B 6/504 382/131 |
| 2011/0130668 | A1* | 6/2011 | Ohyu | A61B 5/0263 600/504 |

OTHER PUBLICATIONS

International Written Opinion mailed Jan. 21, 2014 for PCT/JP2013/078742 filed Oct. 23, 2013.

* cited by examiner

| TISSUE | ANALYSIS (PARAMETER) | BLOOD FLOW AMOUNT (ml/min/100 ml) | . |
|---|---|---|---|
| BRAIN |  |  |  |
|  |  |  |  |
|  |  |  |  |
|  |  |  |  |
| KIDNEY |  |  |  |
|  |  |  |  |
|  |  |  |  |
|  |  |  |  |
| LIVER |  |  |  |
|  |  |  |  |
|  |  |  |  |
|  |  |  |  |
| . |  |  |  |
|  |  |  |  |
|  |  |  |  |
|  |  |  |  |

FIG.5
(A)
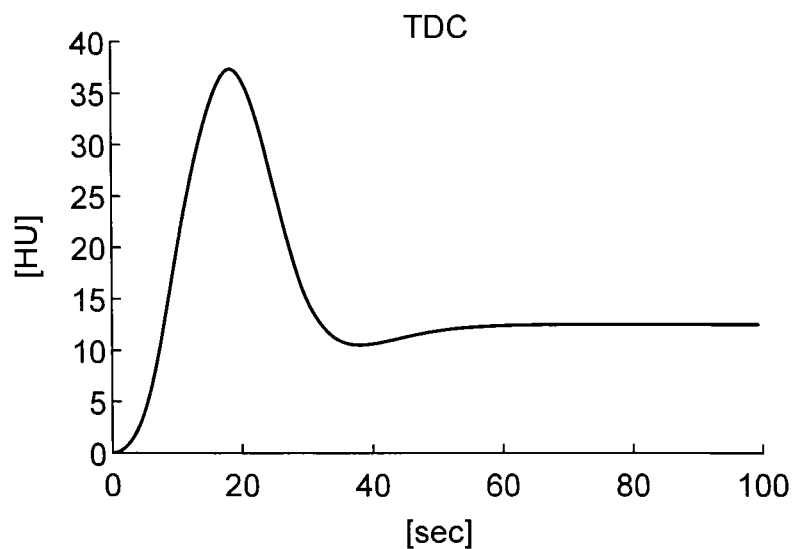
(B)
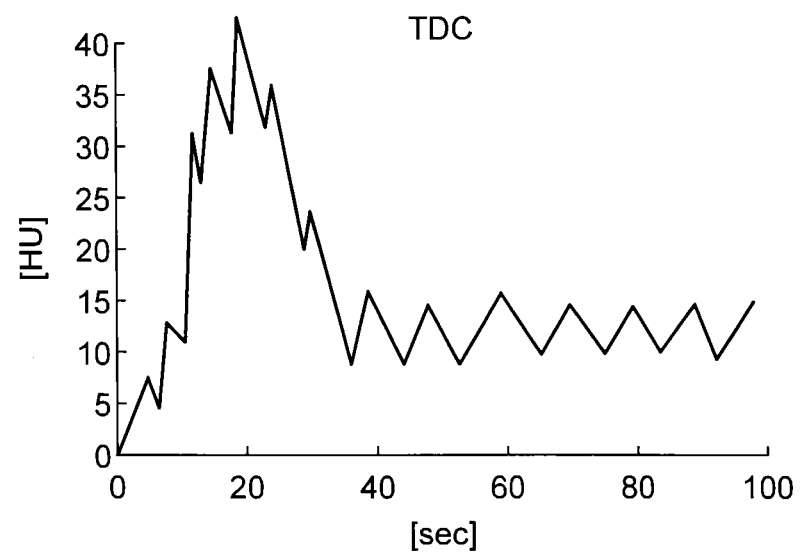

FIG.6
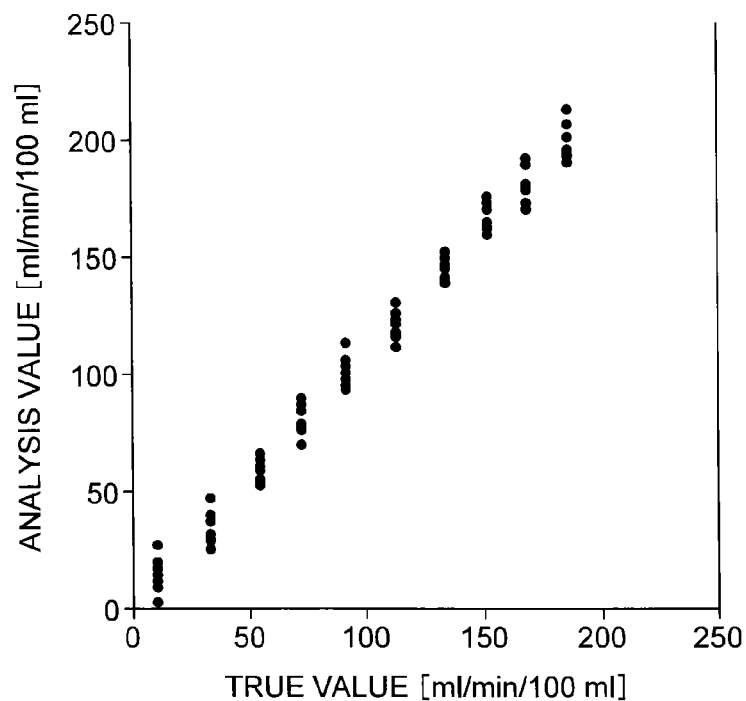
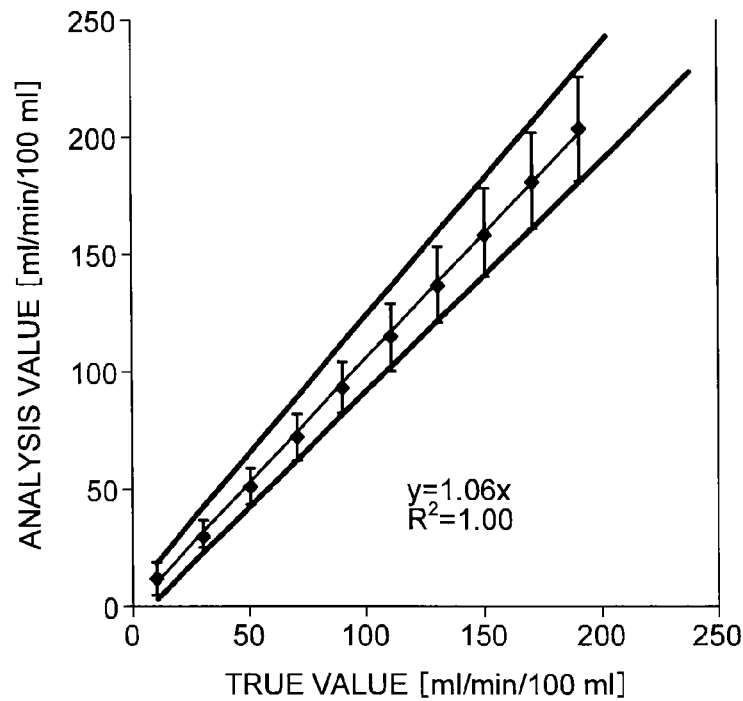

FIG.8
(A) RELIABILITY MAP
(DISPLAYING ENTIRE AREA)
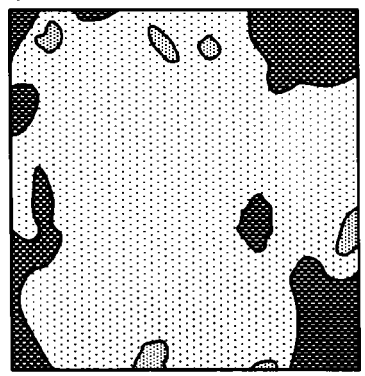
(B) RELIABILITY MAP
(DISPLAYING PARTIAL AREA)
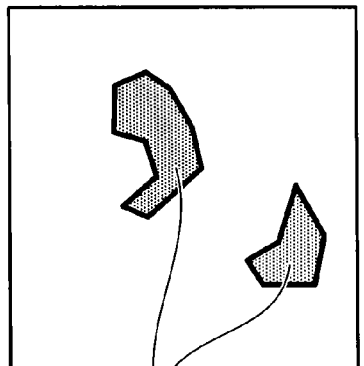
11
(C) PERFUSION IMAGE
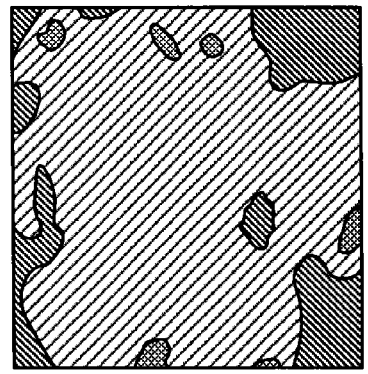
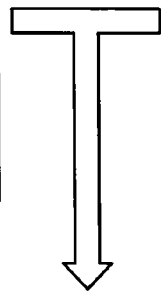
(D) SUPERIMPOSED IMAGE
11

IMAGE PROCESSING APPARATUS, MEDICAL IMAGE DIAGNOSIS APPARATUS, AND IMAGE PROCESSING METHOD

CROSS-REFERENCE TO RELATED APPLICATIONS

This application is a continuation of International Application No. PCT/JP2013/078742, filed on Oct. 23, 2013 which claims the benefit of priority of the prior Japanese Patent Application No. 2012-233609, filed on Oct. 23, 2012, the entire contents of which are incorporated herein by reference.

FIELD

Embodiments described herein relate generally to an image processing apparatus, a medical image diagnosis apparatus, and an image processing method.

BACKGROUND

Conventionally, perfusion images are generated by an X-ray Computed Tomography (CT) apparatus or a Magnetic Resonance Imaging (MRI) apparatus, so as to analyze, for example, dynamics of bloodstream in a brain tissue, a liver tissue, or a pancreas tissue. For example, the X-ray CT apparatus calculates chronological changes in CT values from X-ray CT images that are taken in time series and are of the head or the abdomen of an examined subject (hereinafter, "patient") to whom a nonionic iodine contrast agent has been injected. Further, the X-ray CT apparatus generates a perfusion image in which an index indicating the dynamics of the bloodstream passing through the tissue is mapped on the tissue, on the basis of the calculated chronological changes in the CT values. According to the conventional technique described above, however, it is difficult to check the reliability of analysis results of the perfusion images.

BRIEF DESCRIPTION OF THE DRAWINGS

FIG. 5 is a chart of an example of a noise adding process performed by a generating unit according to the first embodiment;

FIG. 6 is an example of a true value/analysis value chart generated by the generating unit according to the first embodiment;

FIG. 8 is a drawing for explaining a first example of a display controlling process performed by a display control unit according to the first embodiment;

DETAILED DESCRIPTION

According to an embodiment, an image processing apparatus comprising an information obtaining unit, an estimating unit, a generating unit and a display control unit. The information obtaining unit that obtains information about an obstructive factor that is related to a precision level of perfusion images and is contained in a plurality of pieces of medical image data acquired chronologically. The estimating unit that, on a basis of a time density curve indicating a chronological transition of a signal strength at a blood vessel through which blood flows into a tissue serving as an analysis target of which a perfusion state is analyzed from the plurality of pieces of medical image data and on a basis of a perfusion model of the tissue serving as the analysis target, estimates a time density curve at the tissue serving as the analysis target. The generating unit that generates assessment information, on a basis of the time density curve at the tissue serving as the analysis target estimated by the estimating unit and on a basis of the information about the obstructive factor obtained by the information obtaining unit, the assessment information being used for assessing reliability of the perfusion images generated from the plurality of pieces of medical image data. The display control unit that exercises control so that a predetermined display unit displays the assessment information generated by the generating unit.

Figure 1:
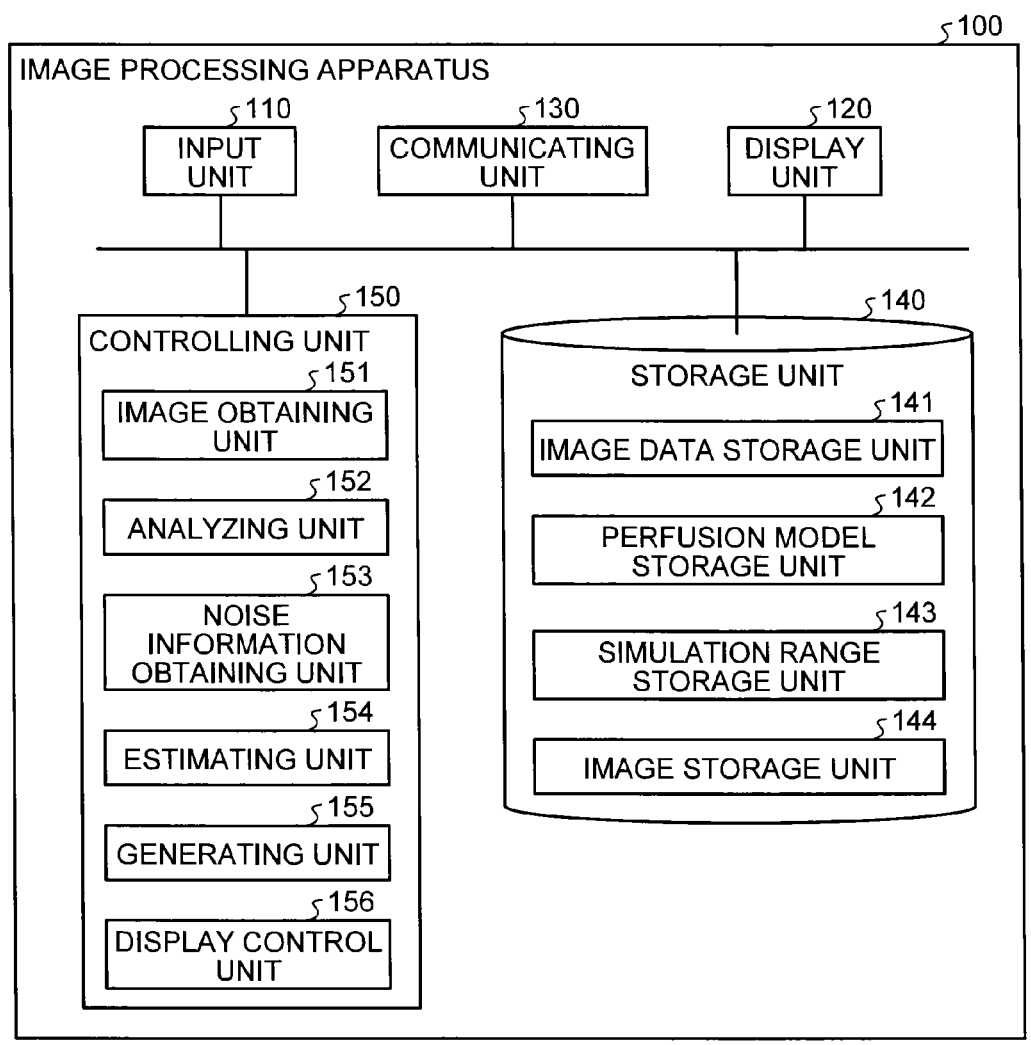
FIG. 1 is a diagram of an exemplary configuration of an image processing apparatus according to a first embodiment.

FIG. 1 is a diagram of an exemplary configuration of an image processing apparatus 100 according to a first embodiment. As illustrated in FIG. 1, the image processing apparatus 100 includes an input unit 110, a display unit 120, a communicating unit 130, a storage unit 140, and a controlling unit 150. For example, the image processing apparatus 100 may be configured with a workstation, an arbitrary personal computer, or the like and is connected to a medical image diagnosis apparatus and an image storing apparatus (not shown) via a network. The medical image diagnosis apparatus may be, for example, an X-ray Computed Tomography (CT) apparatus, a Magnetic Resonance Imaging (MRI) apparatus, or the like. The medical image diagnosis apparatus is capable of generating three-dimensional medical image data (e.g., three-dimensional medical image data of the head or the abdomen that is taken chronologically while the contrast is being enhanced). The image storing apparatus is a database for storing medical images therein. More specifically, the image storing apparatus stores the three-dimensional medical image data transmitted from the medical image diagnosis apparatus into a storage unit, so as to keep the three-dimensional medical image data therein. In the following sections, the three-dimensional medical image data may be referred to as volume data.

The image processing apparatus 100, the medical image diagnosis apparatus, and the image storing apparatus described above are configured to be able to directly or indirectly communicate with one another, via an intra-hospital Local Area Network (LAN) installed in a hospital.

For example, if a Picture Archiving and Communication System (PACS) has been introduced, the apparatuses transmit and receive medical images and the like to and from one another, according to Digital Imaging and Communications in Medicine (DICOM) specifications.

The input unit 110 is configured with a mouse, a keyboard, a trackball, and/or the like and is configured to receive inputs of various types of operations performed on the image processing apparatus 100 from an operator. More specifically, the input unit 110 receives an input of information for obtaining pieces of volume data that correspond to a plurality of phases and that are to be used in a perfusion analysis, from the image storing apparatus. For example, the input unit 110 receives an input for obtaining volume data of the head or the abdomen that is taken chronologically through a dynamic scan performed by an X-ray CT apparatus, the volume data being used for a perfusion analysis.

The display unit 120 is configured with a liquid crystal panel or the like serving as a stereoscopic display monitor and is configured to display various types of information. More specifically, the display unit 120 displays, for example, a Graphical User Interface (GUI) used for receiving various types of operations from the operator, as well as a display image generated through a process performed by the controlling unit 150 (explained later). The display image generated by the controlling unit 150 will be explained later. The communicating unit 130 is configured with a Network Interface Card (NIC) or the like and is configured to communicate with other apparatuses.

As illustrated in FIG. 1, the storage unit 140 includes an image data storage unit 141, a perfusion model storage unit 142, a simulation range storage unit 143, and an image storage unit 144. For example, the storage unit 140 is configured with a hard disk, a semiconductor memory element, or the like and is configured to store various types of information therein. The image data storage unit 141 is configured to store therein the pieces of volume data corresponding to the plurality of phases obtained from the image storing apparatus via the communicating unit 130.

Figures 2, 3:
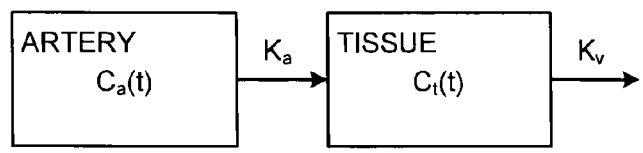
FIG. 2 is a diagram of an example of a perfusion model stored in a perfusion model storage unit according to the first embodiment.
FIG. 3 is a table of examples of simulation ranges stored in a simulation range storage unit according to the first embodiment.

The perfusion model storage unit 142 stores therein perfusion models of a tissue serving as an analysis target. More specifically, the perfusion model storage unit 142 stores therein perfusion models each indicating an inflow and an outflow of blood (a contrast agent) to and from the tissue serving as the analysis target. FIG. 2 is a diagram of an example of a perfusion model stored in the perfusion model storage unit 142 according to the first embodiment. For example, as illustrated in FIG. 2, the perfusion model storage unit 142 stores therein a perfusion model indicating an inflow of blood (the contrast agent) from an artery to the tissue and an outflow of blood (the contrast agent) from the tissue.

In FIG. 2, "$C_a(t)$" denotes a density of the contrast agent at the artery, whereas "$C_t(t)$" denotes a density of the contrast agent at the tissue. Further, "$k_a$" and "$k_v$" in FIG. 2 denote a speed coefficient of the inflow and a speed coefficient of the outflow, respectively. In one example, "$k_a$" and "$k_v$" correspond to an "in-flow" perfusion value and a "mean transit time", respectively. Although FIG. 2 shows a "single-input one compartment model" where the inflow is only from the artery, this is only for an illustration purpose. Alternatively, a "dual-input one compartment model" where there are inflows from an artery and a portal vein may be used, for example. In other words, the perfusion model storage unit 142 stores therein various types of perfusion models, which may arbitrarily be stored therein by a user.

Returning to the description of FIG. 1, the simulation range storage unit 143 stores therein ranges of parameters indicating differences in perfusions, for each of the tissues serving as analysis targets. More specifically, for each of the tissues, the simulation range storage unit 143 stores therein simulation ranges each indicating information about bloodstream expected to be exhibited when a perfusion analysis is performed on the tissue. FIG. 3 is a table of examples of the simulation ranges stored in the simulation range storage unit 143 according to the first embodiment.

For example, as illustrated in FIG. 3, for each of the tissues, the simulation range storage unit 143 stores therein the simulation ranges in each of which an "analysis (parameter)" is kept in correspondence with a "blood flow amount (ml/min/100 ml)". In FIG. 3, the "analysis (parameter)" is a parameter used in the perfusion analysis. Further, the "blood flow amount (ml/min/100 ml)" in FIG. 3 indicates a blood flow amount that flows during a unit time period per unit volume of the tissue, and a range of blood flow amount is stored, for example. In other words, the simulation range storage unit 143 stores therein the simulation ranges each indicating a range of blood flow amount (e.g., 50-80) corresponding to the situation when a predetermined analysis is performed on the tissue.

The image storage unit 144 stores therein image data currently being processed by the controlling unit 150 (explained later), as well as the true value/analysis value chart, a reliability map, and the like generated as a result of processes. The true value/analysis value chart and the reliability map will be explained later.

Returning to the description of FIG. 1, for example, the controlling unit 150 is configured by using an electronic circuit such as a Central Processing Unit (CPU) or a Micro Processing Unit (MPU), or an integrated circuit such as an Application Specific Integrated Circuit (ASIC) or a Field Programmable Gate Array (FPGA), and is configured to exercise overall control of the image processing apparatus 100.

For example, as illustrated in FIG. 1, the controlling unit 150 includes an image obtaining unit 151, an analyzing unit 152, a noise information obtaining unit 153, an estimating unit 154, a generating unit 155, and a display control unit 156. Further, the controlling unit 150 performs the perfusion analysis by using the pieces of volume data corresponding to the plurality of phases and generates the true value/analysis value chart and the reliability map that enable the user to check the reliability of obtained analysis results. In the following sections, an example will be explained in which pieces of volume data taken chronologically by an X-ray CT apparatus will be used as the pieces of volume data corresponding to the plurality of phases.

The image obtaining unit 151 is configured to obtain the pieces of volume data that correspond to the plurality of phases and are to be used in the perfusion analysis from the image storing apparatus (not shown) via the communicating unit 130 and stores the obtained pieces of volume data into the image data storage unit 141. For example, on the basis of information input by the operator via the input unit 110, the image obtaining unit 151 obtains the volume data taken chronologically by the X-ray CT apparatus and stores the obtained volume data into the image data storage unit 141.

The analyzing unit 152 is configured to perform the perfusion analysis by using the pieces of volume data that correspond to the plurality of phases, have been obtained by the image obtaining unit 151, and are stored in the image data storage unit 141. More specifically, the analyzing unit 152 performs the perfusion analysis in accordance with parameter information input by the operator via the input unit 110. For example, the analyzing unit 152 performs the perfusion analysis parameter on a tissue (e.g., the brain, a kidney, or the liver) serving as an analysis target, by using a specified analysis. In one example, the analyzing unit 152 performs an analysis on an analysis parameter cerebral blood perfusion (CBP) that uses a brain tissue as an analysis target.

The noise information obtaining unit 153 is configured to obtain information about an obstructive factor that is related to the precision level of perfusion images and is contained in a plurality of pieces of medical image data acquired chronologically. More specifically, as the information about the obstructive factor related to the precision level of the perfusion images, the noise information obtaining unit 153 obtains information about noise, information about artifacts, or information about body movements contained in the plurality of pieces of medical image data. Alternatively, the noise information obtaining unit 153 obtains information about an obstructive factor that is related to the precision level of the perfusion images and is contained in a plurality of pieces of medical image data acquired chronologically while the contrast is being enhanced by a contrast agent. Further, the noise information obtaining unit 153 obtains information about an obstructive factor related to the precision level of the perfusion images and is contained in a plurality of pieces of three-dimensional medical image data acquired chronologically. In an exemplary embodiment described below, en example will be explained in which the noise information obtaining unit 153 obtains information about noise contained in a plurality of pieces of three-dimensional image data acquired chronologically, while the contrast is being enhanced by a contrast agent.

In the present example, the noise information obtaining unit 153 calculates an image SD of an X-ray CT image generated from the volume data on which the analyzing unit 152 has performed the perfusion analysis.

For example, the noise information obtaining unit 153 calculates noise contained in the volume data by using an arbitrary region in each of the plurality of pieces of volume data. In one example, the noise information obtaining unit 153 calculates the image SD from pixel values (or CT values of voxels corresponding to the pixels) contained in a Region Of Interest (ROI) that is arbitrarily set by the user within the images used for the perfusion analysis.

The estimating unit 154 is configured to, on the basis of a time density curve indicating a chronological transition of the signal strength at a blood vessel through which blood flows into the tissue serving as the analysis target of which the perfusion state is analyzed from the plurality of pieces of medical image data and on the basis of a perfusion model of the tissue serving as the analysis target, estimate a time density curve at the tissue serving as the analysis target. More specifically, for each of the parameters indicating the differences in the perfusions, the estimating unit 154 estimates the time density curve at the tissue serving as the analysis target, on the basis of the time density curve indicating the chronological transition of the signal strength of the contrast agent at the blood vessel through which blood flows into the tissue serving as the analysis target of which the perfusion state is analyzed from a plurality of pieces of three-dimensional medical image data and on the basis of the perfusion model of the tissue serving as the analysis target. For example, the estimating unit 154 estimates the time density curve (TDC) at the tissue, on the basis of a TDC of the blood vessel through which the blood flows into the tissue on which the perfusion analysis was performed by the analyzing unit 152, a perfusion model of the tissue on which the perfusion analysis was performed, and a simulation range corresponding to the tissue on which the perfusion analysis was performed and to an analysis parameter.

Figure 4:
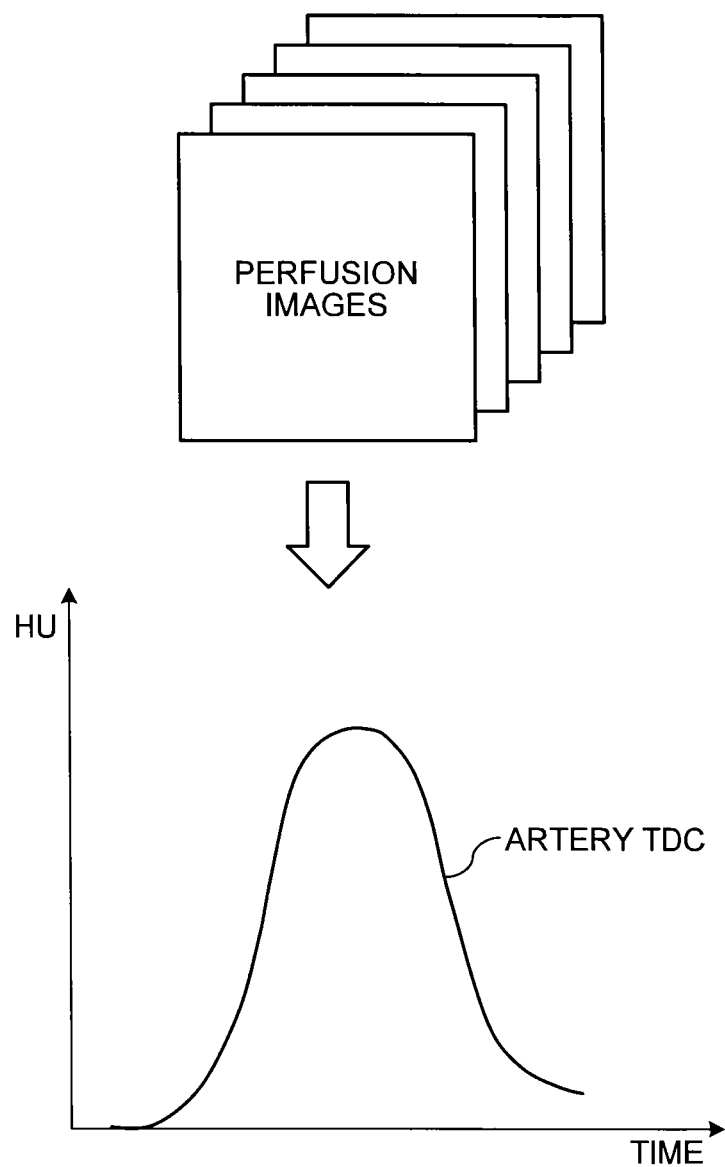
FIG. 4 is a drawing for explaining an example of a process performed by an estimating unit according to the first embodiment.

FIG. 4 is a drawing for explaining an example of a process performed by the estimating unit 154 according to the first embodiment. For example, the estimating unit 154 reads the perfusion model corresponding to the tissue on which the perfusion analysis was performed, from the perfusion model storage unit 142. In one example, the estimating unit 154 reads a perfusion model such as the "single-input one compartment model" illustrated in FIG. 2 and identifies that the inflow blood vessel is an artery.

After that, as illustrated in FIG. 4, the estimating unit 154 obtains an artery TDC on the basis of the X-ray CT images that correspond to the plurality of phases and were used for generating the perfusion images. In an example, from among the pixels in the X-ray CT images corresponding to the plurality of phases, the estimating unit 154 determines that a region in which the pixel values increased at an initial stage (e.g., within a predetermined time period since the first phase) to be a region representing the artery. After that, the estimating unit 154 obtains a TDC of the region determined as the artery. Alternatively, the estimating unit 154 may extract an artery region from the images by performing a pattern matching process or the like so as to obtain a TDC of the extracted region.

After that, the estimating unit 154 estimates the TDC of the tissue on the basis of the obtained TDC of the inflow blood vessel, the perfusion model, and the simulation range corresponding to the tissue serving as the analysis target and to the analysis parameter. For example, the estimating unit 154 estimates the TDC of the tissue (hereinafter, the "tissue TDC") by using Expression (1) shown below. In this situation, Expression (1) is derived from the perfusion model illustrated in FIG. 2. In other words, "$C_t(t)$" in Expression (1) denotes the tissue TDC, whereas "$C_a(t)$" in Expression (1) denotes the artery TDC. Further, in Expression (1), "$k_a$" and "$k_v$" denote an "in-flow perfusion" and a "mean transit time", respectively.

$$\frac{dC_t(t)}{dt} = k_a C_a(t) - k_v C_t(t) \quad (1)$$

As shown in Expression (1), for example, the estimating unit 154 calculates the tissue TDC "$C_t(t)$" (the density of the contrast agent at the tissue) by subtracting the contrast agent flowing out at the speed "$k_v$" from the contrast agent that has flowed into the tissue at the speed "$k_a$" via the artery of which the TDC is "$C_a(t)$".

In this situation, the estimating unit 154 estimates tissue TDCs by varying the values of "$k_a$" and "$k_v$" in accordance with the simulation range (see FIG. 3) stored in the simulation range storage unit 143. In other words, the estimating unit 154 obtains the information about the blood flow amount or the like on the basis of the tissue serving as the analysis target and the analysis parameter and estimates the tissue TDCs by varying the values of "$k_a$" and "$k_v$" within the obtained blood flow amount range. In the following sections, "$k_a$" and "$k_v$" will be referred to as simulation parameters.

Returning to the description of FIG. 1, the generating unit 155 is configured to generate assessment information used for assessing reliability of the perfusion images generated from the plurality of pieces of medical image data, on the basis of the time density curve at the tissue serving as the analysis target estimated by the estimating unit 154 and on the basis of the information about the obstructive factor obtained by the noise information obtaining unit 153. For example, the generating unit 155 generates the assessment information used for assessing the reliability of the perfusion images generated from the plurality of pieces of three-dimensional medical image data, on the basis of the time density curve at the tissue serving as the analysis target estimated by the estimating unit 154 for each of the simulation parameters and on the basis of the noise information obtained by the noise information obtaining unit 153. More specifically, the generating unit 155 adds noise corresponding to the image SD obtained by the noise information obtaining unit 153, to each of the tissue TDCs estimated by the estimating unit 154.

FIG. 5 is a chart of an example of a noise adding process performed by the generating unit 155 according to the first embodiment. FIG. 5 illustrates tissue TDCs. For example, as illustrated in FIG. 5, the generating unit 155 generates a tissue TDC (FIG. 5 (B)) by adding the noise corresponding to the image SD obtained by the noise information obtaining unit 153 to the tissue TDC (FIG. 5 (A)) estimated by the estimating unit 154.

In one example, the generating unit 155 adds the noise by varying the CT value (HU) of the tissue TDC estimated by the estimating unit 154, within a range of CT values (HU) corresponding to the image SD obtained by the noise information obtaining unit 153.

After that, the generating unit 155 causes the analyzing unit 152 to perform a perfusion analysis by using the tissue TDC to which the noise has been added and further generates the assessment information used for assessing the reliability of the perfusion images. More specifically, the generating unit 155 generates a chart indicating an error range for feature values of the perfusion images generated from the plurality of pieces of volume data. Even more specifically, the generating unit 155 generates a true value/analysis value chart obtained by causing a perfusion analysis to be performed on each of the noise-added tissue TDCs and plotting the obtained analysis values into a chart, the tissue TDCs each corresponding to a different one of the simulation parameters and having been estimated by the estimating unit 154.

The analysis parameter used in the perfusion analysis performed by the analyzing unit 152 is the same as the analysis parameter used for the perfusion images of which the reliability is assessed. For example, to generate assess information used for assessing the reliability of perfusion images of which the analysis parameter is CBP, the used analysis parameter is CBP.

FIG. 6 is an example of the true value/analysis value chart generated by the generating unit 155 according to the first embodiment. In FIG. 6, the vertical axis expresses the analysis value (ml/min/100 ml) obtained by performing a perfusion analysis on the noise-added tissue TDCs, whereas the horizontal axis expresses the true value (ml/min/100 ml) used as the simulation parameter.

As shown in the upper section of FIG. 6, for example, the generating unit 155 generates a true value/analysis value chart by plotting analysis values obtained by performing a perfusion analysis on tissue TDCs to each of which noise has been added, the tissue TDCs having been estimated by using ten mutually-different simulation parameters. In other words, to generate the true value/analysis value chart shown in FIG. 6, the estimating unit 154 estimates the tissue TDCs by varying the blood flow amount, which is a simulation parameter, in the ten mutually-different ways. The generating unit 155 then adds noise to each of the tissue TDCs estimated by the estimating unit 154 and causes the perfusion analysis to be performed thereon.

In this situation, as illustrated in the upper section of FIG. 6, the generating unit 155 causes the perfusion analysis to be performed multiple times on any tissue TDC from mutually the same simulation parameter, for the purpose of ensuring that a fluctuation tendency caused by the noise is accurately reflected in the analysis values from mutually the same simulation parameter. In one example, the generating unit 155 causes the perfusion analysis to be performed forty times, for each simulation parameter. In other words, the generating unit 155 repeatedly performs the noise adding process and the perfusion analysis process forty times on each of the tissue TDCs estimated by the estimating unit 154 and further plots the analysis values into the chart.

The generating unit 155 generates the true value/analysis value chart as shown in the upper section of FIG. 6, by performing the processes described above on each of all the simulation parameters. After that, when having generated the true value/analysis value chart, the generating unit 155 performs a statistical processing process on the obtained results. For example, the generating unit 155 calculates an average value of the analysis values, a standard deviation, and/or an error from the true value in correspondence with each of the simulation parameters. In one example, as shown in the lower section of FIG. 6, the generating unit 155 calculates an "average value±standard deviation value" and sets an area positioned within the standard deviation as a valid range.

In this situation, the valid range refers to a range of true values that can be realized in correspondence with analysis values. For example, if an analysis value is "200 (ml/min/100 ml)", the true value is in the range of "160-210 (ml/min/100 ml)". In other words, when the true value is in the range of "160-210", the analysis value can be calculated as "200".

The generating unit 155 generates the true value/analysis value chart as described above. For example, by referring to the chart shown in the lower section of FIG. 6, the user is able to observe the following: the larger the analysis value is, the larger is the standard deviation and the lower is the reliability.

Figure 7:
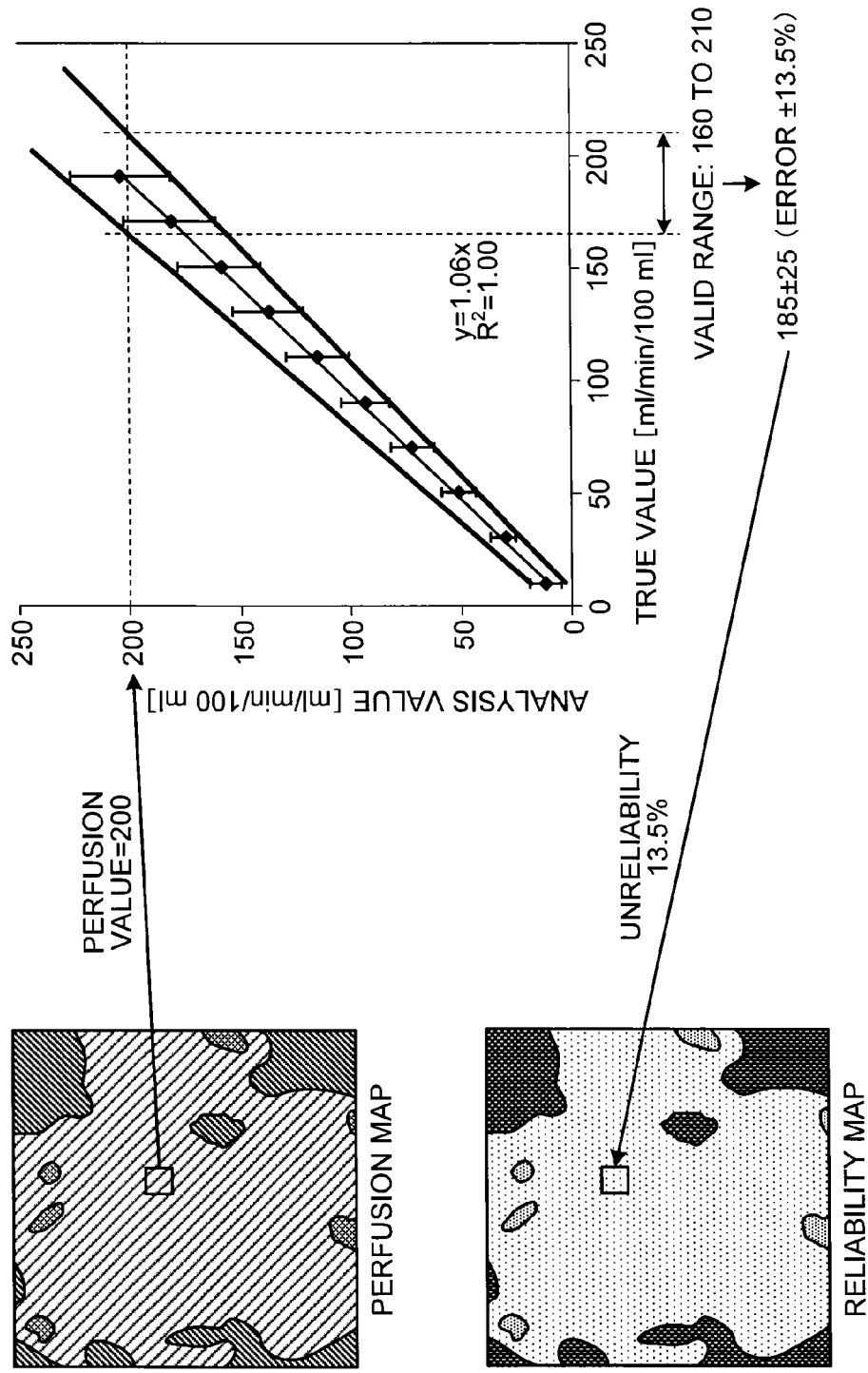
FIG. 7 is a drawing for explaining an example of a reliability map generating process performed by the generating unit according to the first embodiment.

Further, the generating unit 155 calculates an error in the feature value at each of the pixels in the perfusion images by using the true values/analysis values and further generates a reliability display image indicating the calculated errors. FIG. 7 is a drawing for explaining an example of a reliability map generating process performed by the generating unit 155 according to the first embodiment. For example, as illustrated in FIG. 7, the generating unit 155 obtains a "valid range: 160-210" from the true value/analysis value chart, with respect to a pixel of which the perfusion value is "200" in the perfusion image (a perfusion map).

After that, with respect to the obtained "valid range: 160-210", the generating unit 155 calculates an average value "185=(160+210)/2" and a valid range width "150=210-160". Further, on the basis of the calculated average value and the calculated valid range width, the generating unit 155 calculates a true value "185±25" corresponding to the analysis value "200" and calculates an error "±13.5% (=25/185×100)".

In other words, the generating unit 155 calculates the true value of the pixel having an analysis value of "200" as "185±25" and calculates the error as "±13.5%". In this situation, the reliability of perfusion images becomes higher, as the error of the true value becomes smaller. Accordingly, the error "±13.5%" may be expressed as unreliability "13.5%", as illustrated in FIG. 7.

Further, as illustrated in FIG. 7, by performing the process described above on each of all the pixels in the perfusion images, the generating unit 155 calculates an error (i.e., unreliability) of each pixel and generates a reliability map in which the difference in the calculated unreliability levels is expressed in color. In this situation, the reliability map generated by the generating unit 155 may express the difference in the unreliability levels by using different levels of darkness of a single color or may express the difference in the unreliability levels by using a plurality of colors.

Further, when generating the reliability map, the generating unit 155 generates a reliability map indicating only one or more areas in which the calculated error exceeds a predetermined value. In this situation, the generating unit 155 uses "5%" as the predetermined value, for example, and generates a reliability map indicating only such an area in which the unreliability exceeds "5%" in the perfusion image.

Returning to the description of FIG. 1, the display control unit 156 exercises control so that the display unit 120 displays the assessment information generated by the generating unit 155. More specifically, the display control unit 156 exercises control so that the display unit 120 displays one or both of the reliability map generated by the generating unit 155 and a superimposed image in which the reliability map is superimposed on the perfusion images. Further, the display control unit 156 exercises control so that the display unit 120 displays the true value/analysis value chart.

FIG. 8 is a drawing for explaining a first example of the display controlling process performed by the display control unit 156 according to the first embodiment. FIG. 8(A) illustrates a reliability map (displaying the entire area); FIG. 8(B) illustrates a reliability map (displaying a partial area); and FIG. 8(C) illustrates a perfusion image. In other words, FIG. 8(A) illustrates the reliability map (displaying the entire area) obtained by acquiring a valid range for each of all the pixels in the perfusion image from the true value/analysis value chart, calculating an error (the unreliability) of each of the pixels, and expressing each of the pixels with a color corresponding to the calculated error (the unreliability). FIG. 8(B) illustrates the reliability map (displaying a partial area) obtained by extracting areas 11 where the error (the unreliability) exceeds a predetermined value from the reliability map (displaying the entire area) and displaying only the areas 11. In one example, the areas 11 are areas where the error (the unreliability) exceeds "5%". Further, FIG. 8(C) illustrates the analyzed perfusion image.

For example, as illustrated in FIG. 8(D), the display control unit 156 causes the display unit 120 to display a superimposed image in which the reliability map (displaying the partial area) showing the areas 11 where the unreliability exceeds the predetermined value is superimposed on the perfusion image. As a result, the user is able to recognize, at a glance, the areas where the unreliability is high (i.e., where the reliability is low) in the perfusion image. For example, the reliability map (displaying the partial area) is a reliability map showing only the areas where the unreliability exceeds "5%" in the perfusion image.

Further, the display control unit 156 causes the display unit 120 to display one or more images specified by the user either individually or while being arranged side by side, from among the reliability map (displaying the entire area) illustrated in FIG. 8(A), the reliability map (displaying the partial area), and the superimposed image in which the reliability map (displaying the partial area) is superimposed on the reliability map (displaying the entire area).

Figure 9:
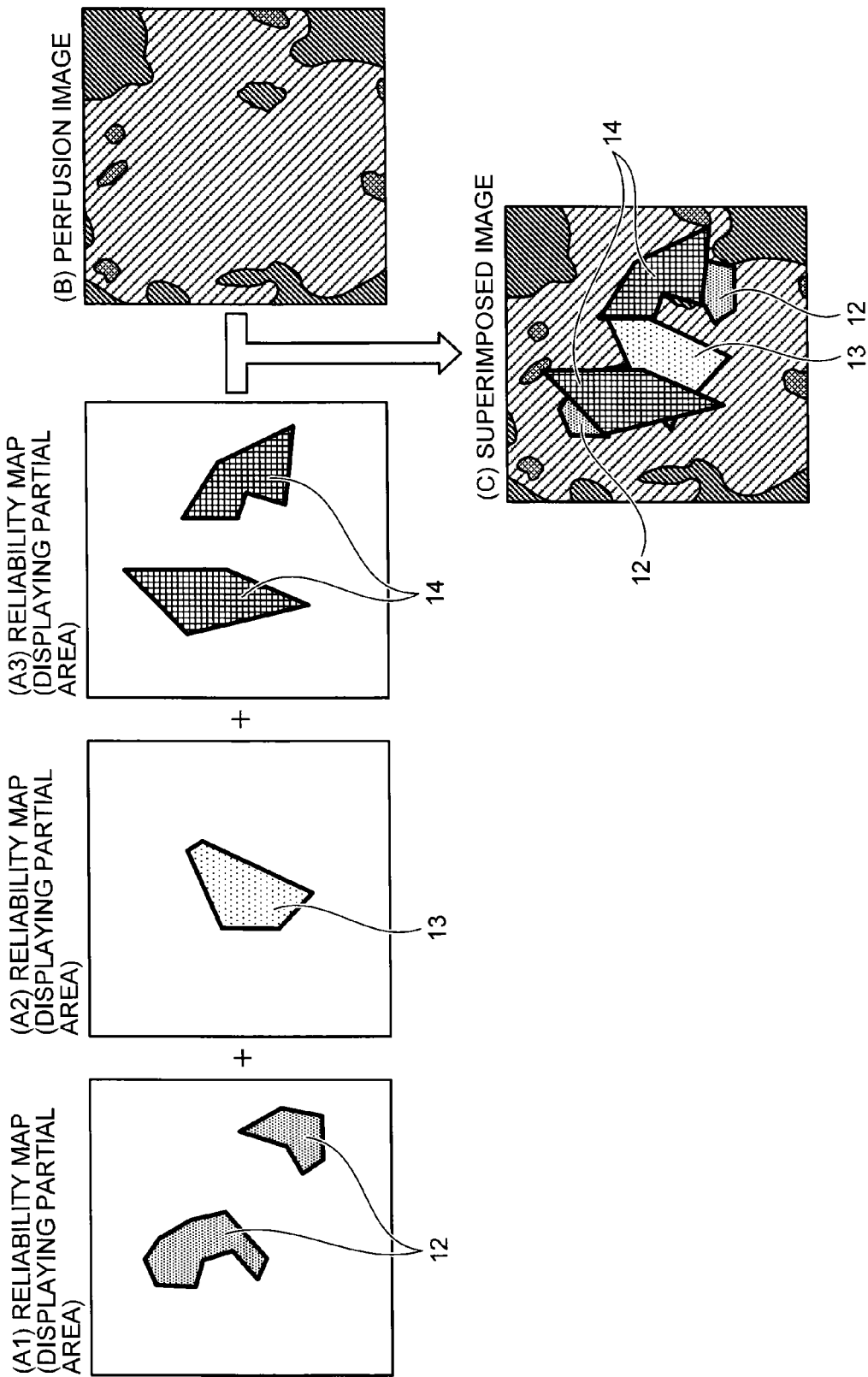
FIG. 9 is a drawing for explaining a second example of the display controlling process performed by the display control unit according to the first embodiment.

Further, the display control unit 156 causes the display unit 120 to display a reliability map in a superimposed manner, the reliability map being generated from each of the analysis results of the perfusion image obtained by analyzing mutually the same X-ray CT image by using a plurality of analysis parameters. FIG. 9 is a drawing for explaining a second example of the display controlling process performed by the display control unit 156 according to the first embodiment. FIGS. 9(A1), 9(A2), 9(A3) illustrate reliability maps (each displaying a partial area) of a perfusion image analyzed by using mutually-different analysis parameters, whereas FIG. 9(B) illustrates the perfusion image.

In other words, FIG. 9(A1) illustrates the reliability map (displaying a partial area) obtained by calculating the unreliability for each of all the pixels in the perfusion image resulting from an analysis performed on an X-ray CT image while using a predetermined analysis parameter (e.g., a CBP) and displaying only areas 12 where the calculated unreliability exceeds a predetermined value. Further, FIG. 9(A2) illustrates the reliability map (displaying a partial area) obtained by calculating the unreliability for each of all the pixels in the perfusion image resulting from an analysis performed on the same X-ray CT image as the one analyzed in FIG. 9(A1) while using an analysis parameter (e.g., a cerebral blood volume [CBV]) that is different from the one used in FIG. 9(A1) and displaying only an area 13 where the calculated unreliability exceeds the predetermined value. FIG. 9(A3) illustrates the reliability map (displaying a partial area) obtained by calculating the unreliability for each of all the pixels in the perfusion image resulting from an analysis performed on the same X-ray CT image as those analyzed in FIGS. 9(A1) and 9(A2) while using an analysis parameter (e.g., a cerebral blood flow [CBF]) that is different from those used in FIGS. 9(A1) and 9(A2) and displaying only areas 14 where the calculated unreliability exceeds the predetermined value. The perfusion image shown in FIG. 9(B) may be any of the perfusion images for which the reliability maps (each displaying a partial area) shown in FIGS. 9(A1) to 9(A3) are generated.

For example, as illustrated in FIG. 9(C), the display control unit 156 causes the display unit 120 to display a superimposed image in which the areas 12 where the unreliability exceeds the predetermined value with the analysis parameter in FIG. 9(A1), the area 13 where the unreliability exceeds the predetermined value with the analysis parameter in FIG. 9(A2), and the areas 14 where the unreliability exceeds the predetermined value with the analysis parameter in FIG. 9(A3) are superimposed on the perfusion image at the same time. As a result, the user is able to recognize, at a glance, areas having low reliability with all the analysis parameters and, conversely, areas having high reliability with all the analysis parameters.

Figure 10:
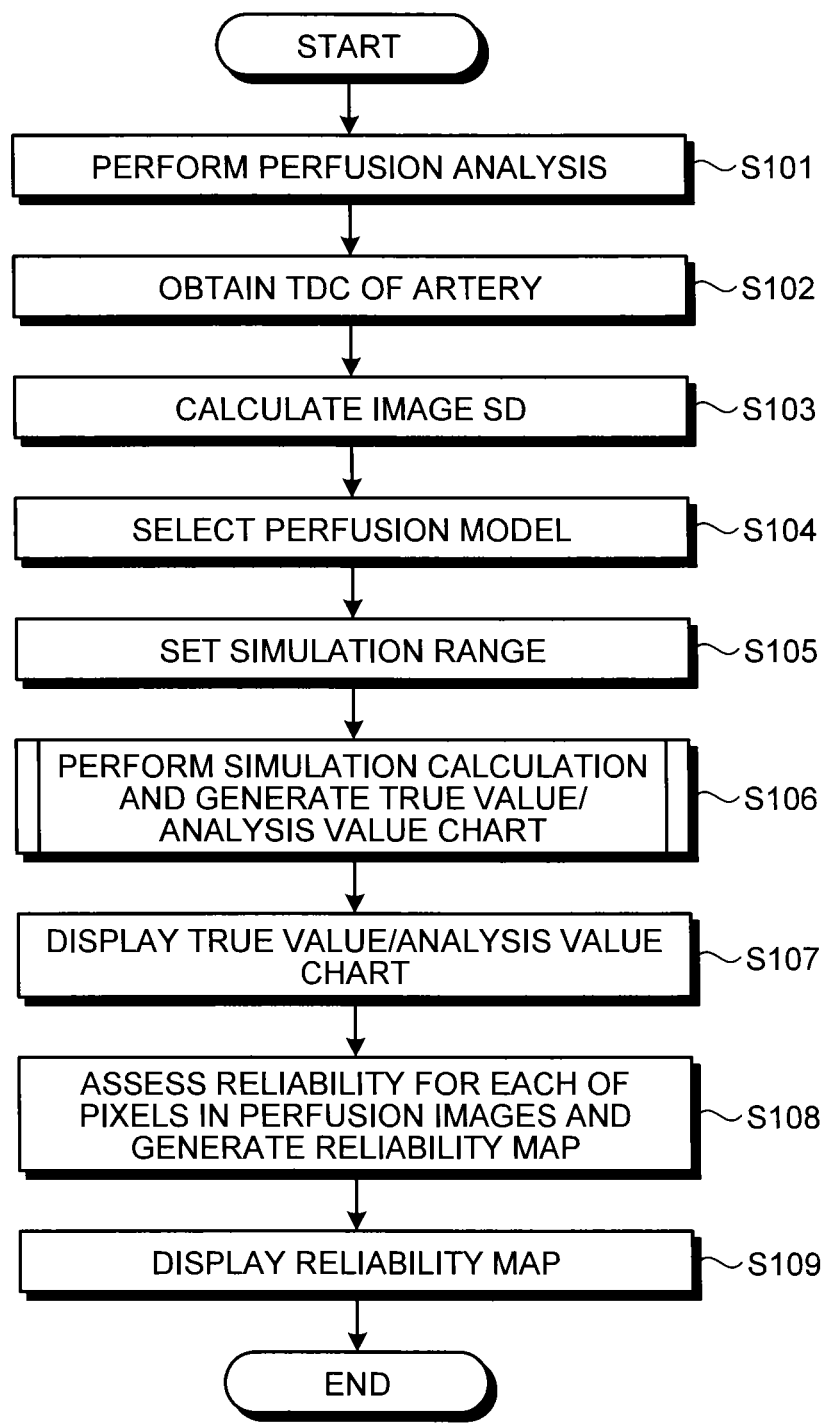
FIG. 10 is a flowchart of a procedure in an overall processing process performed by the image processing apparatus according to the first embodiment.
Figure 11:
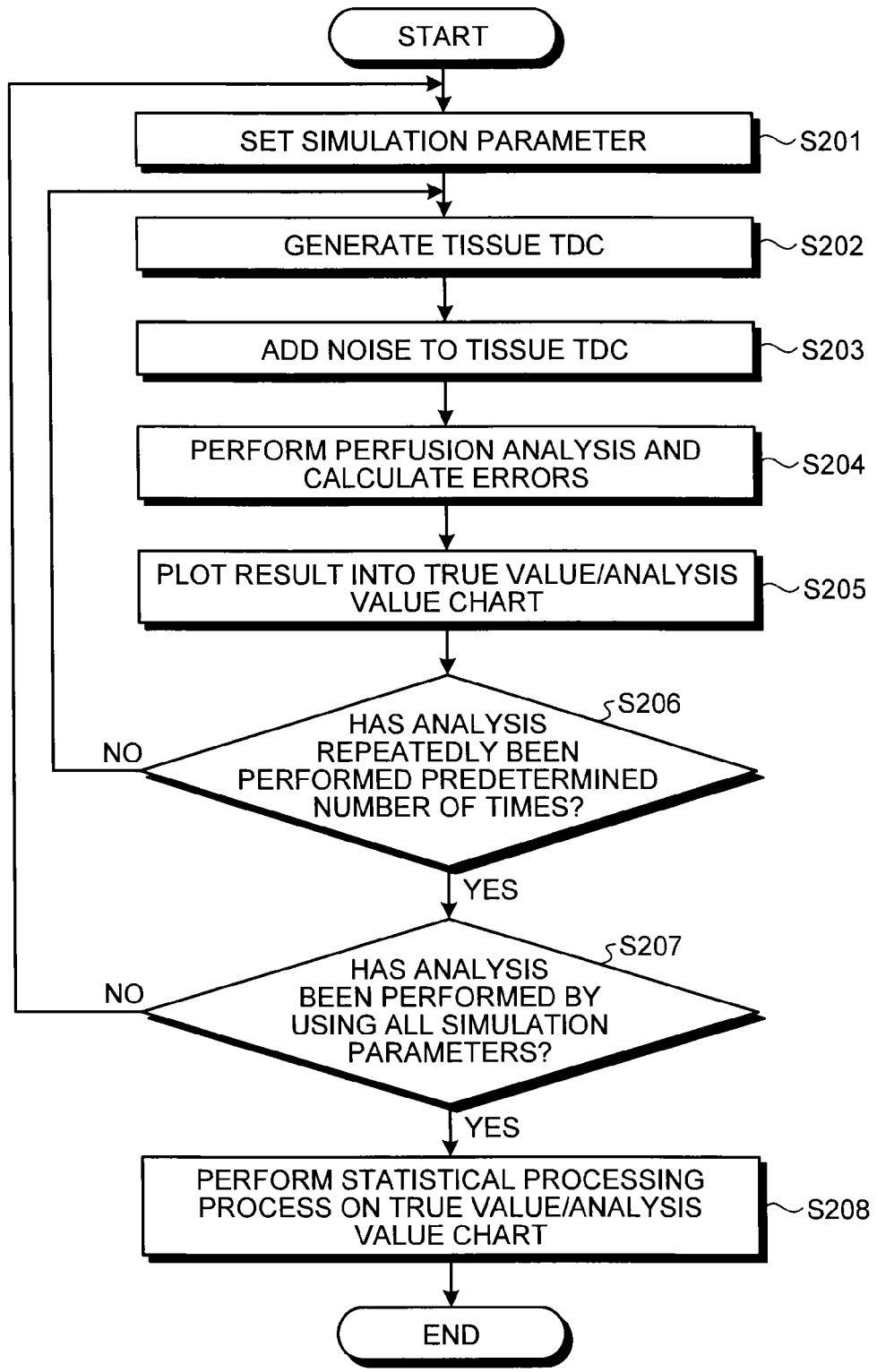
FIG. 11 is a flowchart of a procedure in a true value/analysis value chart generating process performed by the image processing apparatus according to the first embodiment.

Next, a process performed by the image processing apparatus 100 according to the first embodiment will be explained, with reference to FIGS. 10 and 11. First, a procedure in an overall processing process performed by the image processing apparatus 100 will be explained. FIG. 10 is a flowchart of the procedure in the overall processing process performed by the image processing apparatus 100 according to the first embodiment. FIG. 10 illustrates a process that is performed after images have been generated from a plurality of pieces of volume data acquired chronologically while the contrast is being enhanced and the image obtaining unit 151 has obtained the generated images.

As shown in FIG. 10, in the image processing apparatus 100 according to the first embodiment, when the image obtaining unit 151 has obtained the images, the analyzing unit 152 performs a perfusion analysis by using an analysis parameter specified by the user (step S101). After that, the estimating unit 154 obtains a TDC of the artery from the images obtained by the image obtaining unit 151 (step S102), and the noise information obtaining unit 153 calculates an image SD (step S103).

After that, the estimating unit 154 selects a perfusion model (step S104), and obtains a simulation parameter range by referring to the simulation range (step S105). Subsequently, the generating unit 155 performs a simulation calculation by using the tissue TDCs estimated by the estimating unit 154 and generates a true value/analysis value chart (step S106).

The display control unit 156 causes the display unit 120 to display the true value/analysis value chart generated by the generating unit 155 (step S107). After that, the generating unit 155 generates a reliability map by assessing the reliability of each of the pixels in the perfusion images (step S108). The display control unit 156 causes the display unit 120 to display the generated reliability map (step S109).

In the exemplary process shown in FIG. 10, the example is explained in which, after the true value/analysis value chart is displayed, the reliability map is generated and displayed. However, possible embodiments are not limited to this example. Alternatively, another arrangement is acceptable in which, for example, after the true value/analysis value chart and the reliability map have been generated, the chart and the map are displayed while being arranged side by side.

Next, a process to generate the true value/analysis value chart will be explained. FIG. 11 is a flowchart of a procedure in the true value/analysis value chart generating process performed by the image processing apparatus 100 according to the first embodiment. The process shown in FIG. 11 corresponds to the process at step S106 shown in FIG. 10.

As illustrated in FIG. 10, in the image processing apparatus 100 according to the first embodiment, when the simulation parameter range has been obtained, the estimating unit 154 sets a simulation parameter (step S201), and generates (estimates) a tissue TDC (step S202). After that, the generating unit 155 adds noise to the generated tissue TDC (step S203) and causes the analyzing unit 152 to perform a perfusion analysis so as to calculate errors (step S204).

After that, the generating unit 155 plots the analysis values into a true value/analysis value chart (step S205) and judges whether the analysis has repeatedly been performed a predetermined number of times (step S206). If it has been determined that the analysis has not repeatedly been performed the predetermined number of times (step S206: No), the process returns to step S202 where the estimating unit 154 generates a tissue TDC by using the same simulation parameter.

On the contrary, if it has been determined that the analysis has repeatedly been performed the predetermined number of times (step S206: Yes), the generating unit 155 judges whether the analysis has been performed by using all the simulation parameters (step S207). If it has been determined that the analysis has not been performed by using all the simulation parameters (step S207: No), the process returns to step S201, where the estimating unit 154 sets a simulation parameter with which the analysis has not yet been performed.

On the contrary, if it has been determined that the analysis has been performed by using all the simulation parameters (step S207: Yes), the generating unit 155 performs a statistical processing process on the true value/analysis value chart (step S208), and the true value/analysis value chart generating process is thus ended.

As explained above, according to the first embodiment, the noise information obtaining unit 153 obtains the information about the noise contained in the plurality of pieces of volume data acquired chronologically while the contrast is being enhanced by the contrast agent. After that, on the basis of the TDC indicating the chronological transition of the signal strength of the contrast agent at the blood vessel through which the blood flows into the tissue serving as the analysis target of which the perfusion state is analyzed from the plurality of pieces of volume data and on the basis of the perfusion model of the tissue serving as the analysis target, the estimating unit 154 estimates the TDC at the tissue serving as the analysis target for each of the simulation parameters indicating the differences in the perfusions. Further, on the basis of the TDC at the tissue serving as the analysis target estimated by the estimating unit 154 for each of the simulation parameters and on the basis of the noise information obtained by the noise information obtaining unit 153, the generating unit 155 generates the assessment information used for assessing the reliability of the perfusion images generated from the plurality of pieces of volume data. After that, the display control unit 156 exercises control so that the display unit 120 displays the assessment information generated by the generating unit 155. Accordingly, the image processing apparatus 100 according to the first embodiment is able to provide the reliability assessment information in which the TDCs of the inflow blood vessel and the tissue and the noise in the image are taken into consideration. The image processing apparatus 100 thus makes it possible for the user to check the reliability of the analysis results of the perfusion images.

Further, according to the first embodiment, the generating unit 155 generates the chart indicating the error range of the perfusion values in the perfusion images generated from the plurality of pieces of volume data. Accordingly, the image processing apparatus 100 according to the first embodiment makes it possible to provide the information with which it is possible to easily check the reliability of the perfusion images.

Further, according to the first embodiment, the generating unit 155 calculates the error in the perfusion value at each of the pixels in the perfusion images by using the true value/analysis value chart and generates the reliability map indicating the calculated errors. Accordingly, the image processing apparatus 100 according to the first embodiment makes it possible to check the reliability at a glance.

Furthermore, according to the first embodiment, when generating the reliability map, the generating unit 155 generates the reliability map (displaying the partial area) that indicates only the one or more areas where the calculated error exceeds the predetermined value. Accordingly, the image processing apparatus 100 according to the first embodiment makes it possible to recognize, at a glance, the areas having low reliability.

Furthermore, according to the first embodiment, the display control unit 156 exercises control so that the display unit 120 displays one or both of the reliability map generated by the generating unit 155 and the superimposed image in which the reliability map is superimposed on the perfusion image. Accordingly, the image processing apparatus 100 according to the first embodiment makes it possible to recognize the areas having low reliability even more easily.

The first embodiment has thus been explained. The disclosure herein may be carried out in various embodiments other than those described in the first embodiment.

In the first embodiment described above, the example is explained in which the true value/analysis value chart and the images (the perfusion image, the reliability map, and/or the like) are displayed individually or while being arranged side by side. However, possible embodiments are not limited to this example. For instance, it is also possible to display a relationship between the true value/analysis value chart and the images.

Figure 12:
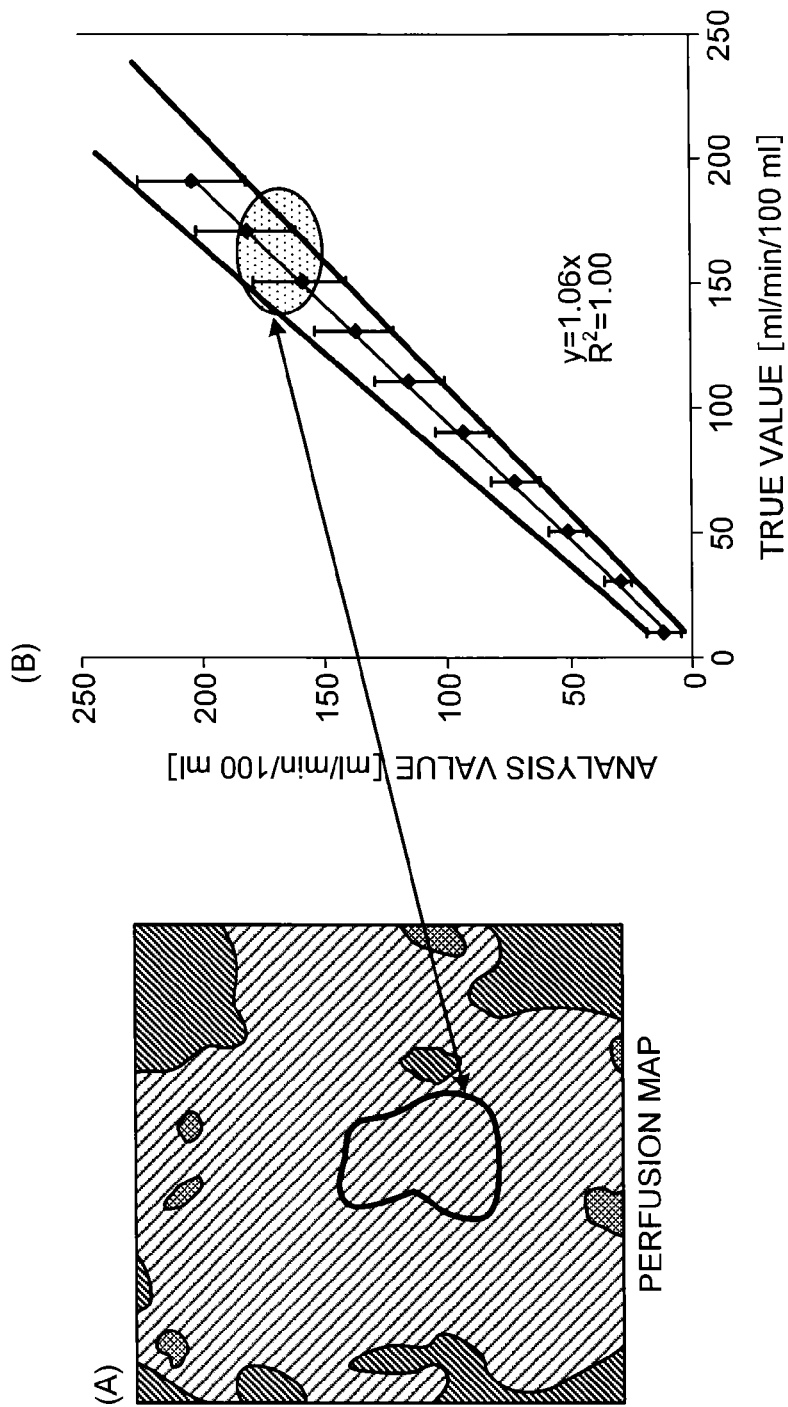
FIG. 12 is a drawing of an example of a display controlling process performed by a display control unit according to a second embodiment.

In that situation, the display control unit 156 exercises control so that the display unit displays a correspondence relationship between an area included in the perfusion image, the reliability map (displaying the entire area), the reliability map (displaying the partial area), or the superimposed image and an area in the true value/analysis value chart. FIG. 12 is a drawing of an example of the display controlling process performed by the display control unit 156 according to a second embodiment. FIG. 12 illustrates an example in which a correspondence relationship between a perfusion image and a true value/analysis value chart is indicated.

For example, as illustrated in FIG. 12, the display control unit 156 exercises control so that the display unit 120 displays the area in the true value/analysis value chart that corresponds to an area in the perfusion image. As a result, for example, the user is able to specify a desired area in the perfusion image and to recognize, at a glance, where the specified area is approximately positioned in the true value/analysis value chart.

In the first embodiment described above, the example is explained in which the image processing apparatus 100 is connected to the medical image diagnosis apparatus and the image storing apparatus via the network and is configured to obtain the images via the communicating unit. However, possible embodiments are not limited to this example. For instance, the exemplary embodiments are also applicable to a situation where the image data desired by the operator is stored into the storage unit 140 via a storage medium such as a flexible disk (FD), a Compact Disk Read-Only Memory (CD-ROM), a Magneto-Optical (MO) disk, or a Digital Versatile Disk (DVD). Alternatively, the exemplary embodiments are also applicable to a situation where a storage device storing therein the image data desired by the operator is provided besides the storage unit 140.

In the first embodiment described above, the example is explained in which the X-ray CT images taken by the X-ray CT apparatus are used. However, possible embodiments are not limited to this example. For instance, it is also acceptable to use MR images taken by an MRI apparatus.

Further, the configuration of the image processing apparatus 100 described in the first embodiment above is merely an example, and the constituent elements thereof may be integrated or separated as appropriate. For example, it is possible to integrate the noise information obtaining unit 153 and the estimating unit 154 together. It is also possible to separate the generating unit 155 into a noise adding unit configured to add the noise and an information generating unit configured to generate the true value/analysis value chart and the reliability maps.

In the first embodiment described above, the example is explained in which the noise contained in the image data is used as the obstructive factor related to the precision level of the perfusion images. However, possible embodiments are not limited to this example. For instance, information about artifacts or information about body movements contained in the image data may be used as the obstructive factor related to the precision level of the perfusion images. In this situation, the information about body movements is, for example, information indicating that, while multiple images in mutually the same position are supposed to be taken, the image taking position varies significantly because the patient did not hold his/her breath properly. When the information about artifacts or the information about body movements is used as described above, an image SD is calculated and the same processes are performed, in the same manner as when the noise is used.

In the first embodiment described above, the example is explained in which the plurality of medical images taken chronologically while the contrast is being enhanced by the contrast agent are used. However, possible embodiments are not limited to this example. For instance, it is acceptable to use a plurality of medical images taken chronologically in a state where the contrast is not being enhanced (hereinafter, a "contrast-unenhanced state"). In that situation, the noise information obtaining unit 153 obtains information about an obstructive factor that is related to the precision level of the perfusion images and is contained in the plurality of pieces of medical image data taken chronologically in the contrast-unenhanced state. On the basis of a time density curve indicating a chronological transition of the signal strength in the contrast-unenhanced state at the blood vessel through which blood flows into the tissue serving as the analysis target and on the basis of the perfusion model of the tissue serving as the analysis target, the estimating unit 154 estimates a time density curve at the tissue serving as the analysis target. Examples of contrast-unenhanced images include MR images that are taken while blood is considered as an intrinsic contrast agent, while performing contrast-unenhanced Magnetic Resonance Angiography (MRA).

In the first embodiment described above, the example is explained in which the image processing apparatus 100 performs the processes on the plurality of pieces of medical image data. However, possible embodiments are not limited to this example. Alternatively, the processes may be performed by a medical image diagnosis apparatus such as an X-ray CT apparatus, an MRI apparatus, am ultrasound diagnosis apparatus, or an X-ray diagnosis apparatus, for example. In that situation, for example, the medical image diagnosis apparatus includes the controlling unit 150 and is configured to perform the various types of processes described above.

As explained above, the image processing apparatus, the medical image diagnosis apparatus, and the image processing method according to at least one aspect of the first and the second embodiments make it possible to check the reliability of the analysis results of the perfusion images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
an information obtaining unit that obtains information about an obstructive factor that is related to a precision level of perfusion images and is contained in a plurality of pieces of medical image data acquired chronologically;
an estimating unit that, on a basis of a time density curve indicating a chronological transition of a signal strength at a blood vessel through which blood flows into a tissue serving as an analysis target of which a perfusion state is analyzed from the plurality of pieces of medical image data and on a basis of a perfusion model of the tissue serving as the analysis target, estimates a time density curve at the tissue serving as the analysis target;
a generating unit that generates assessment information, on a basis of the time density curve at the tissue serving as the analysis target estimated by the estimating unit and on a basis of the information about the obstructive factor obtained by the information obtaining unit, the assessment information being used for assessing reliability of the perfusion images generated from the plurality of pieces of medical image data; and
a display control unit that exercises control so that a predetermined display unit displays the assessment information generated by the generating unit.

2. The image processing apparatus according to claim 1, wherein the generating unit generates a chart indicating an error range for a feature value of the perfusion images generated from the plurality of pieces of medical image data.

3. The image processing apparatus according to claim 2, wherein the generating unit calculates an error in the feature value at each of pixels in the perfusion images by using the chart and generates a reliability display image indicating the calculated errors.

4. The image processing apparatus according to claim 3, wherein, when generating the reliability display image, the generating unit generates a partial reliability display image indicating only one or more areas in which the calculated error exceeds a predetermined value.

5. The image processing apparatus according to claim 3, wherein the display control unit exercises control so that the predetermined display unit displays one or both of the reliability display image generated by the generating unit and a superimposed image in which the reliability display image is superimposed on the perfusion images.

6. The image processing apparatus according to claim 5, wherein the display control unit exercises control so that the predetermined display unit displays a correspondence relationship between an area included in the perfusion images, the reliability display image, the partial reliability display image, or the superimposed image and an area in the chart.

7. The image processing apparatus according to claim 1, wherein, as the information about the obstructive factor related to the precision level of the perfusion images, the information obtaining unit obtains information about noise, information about an artifact, or information about a body movement contained in the plurality of pieces of medical image data.

8. The image processing apparatus according to claim 1, wherein
the information obtaining unit obtains the information about the obstructive factor that is related to the precision level of the perfusion images and is contained in the plurality of pieces of medical image data acquired chronologically while a contrast is being enhanced by a contrast agent, and
on the basis of the time density curve indicating the chronological transition of the signal strength of the contrast agent at the blood vessel through which the blood flows into the tissue serving as the analysis target and on the basis of the perfusion model of the tissue serving as the analysis target, the estimating unit estimates the time density curve at the tissue serving as the analysis target.

9. The image processing apparatus according to claim 1, wherein
the information obtaining unit obtains the information about the obstructive factor that is related to the precision level of the perfusion images and is contained in the plurality of pieces of medical image data acquired chronologically in a state where a contrast is not being enhanced, and
on the basis of the time density curve indicating the chronological transition of the signal strength in the contrast-unenhanced state at the blood vessel through which the blood flows into the tissue serving as the analysis target and on the basis of the perfusion model of the tissue serving as the analysis target, the estimating unit estimates the time density curve at the tissue serving as the analysis target.

10. The image processing apparatus according to claim 1, wherein
the information obtaining unit obtains the information about the obstructive factor that is related to the precision level of the perfusion images and is contained in the plurality of pieces of medical image data that are three-dimensional and are acquired chronologically,
on the basis of the time density curve indicating the chronological transition of the signal strength at the blood vessel through which the blood flows into the tissue serving as the analysis target of which the perfusion state is analyzed from the plurality of pieces of three-dimensional medical image data and on the basis of the perfusion model of the tissue serving as the analysis target, the estimating unit estimates the time density curve at the tissue serving as the analysis target, and
on the basis of the time density curve at the tissue serving as the analysis target estimated by the estimating unit and on the basis of the information about the obstructive factor obtained by the information obtaining unit, the generating unit generates the assessment information used for assessing the reliability of the perfusion images generated from the plurality of pieces of three-dimensional medical image data.

11. A medical image diagnosis apparatus comprising:
an acquiring unit that acquires a plurality of pieces of medical image data that are chronological;
an information obtaining unit that obtains information about an obstructive factor that is related to a precision level of perfusion images and is contained in the plurality of pieces of medical image data acquired by the acquiring unit;
an estimating unit that, on a basis of a time density curve indicating a chronological transition of a signal strength at a blood vessel through which blood flows into a tissue serving as an analysis target of which a perfusion state is analyzed from the plurality of pieces of medical image data and on a basis of a perfusion model of the tissue serving as the analysis target, estimate a time density curve at the tissue serving as the analysis target;
a generating unit that generates assessment information, on a basis of the time density curve at the tissue serving as the analysis target estimated by the estimating unit and on a basis of the information about the obstructive factor obtained by the information obtaining unit, the assessment information being used for assessing reliability of the perfusion images generated from the plurality of pieces of medical image data; and a display control unit that exercises control so that a predetermined display unit displays the assessment information generated by the generating unit.

12. An image processing method implemented by an image processing apparatus, the image processing method comprising:

obtaining information about an obstructive factor that is related to a precision level of perfusion images and is contained in a plurality of pieces of medical image data acquired chronologically;

on a basis of a time density curve indicating a chronological transition of a signal strength at a blood vessel through which blood flows into a tissue serving as an analysis target of which a perfusion state is analyzed from the plurality of pieces of medical image data and on a basis of a perfusion model of the tissue serving as the analysis target, estimating a time density curve at the tissue serving as the analysis target;

on a basis of the time density curve at the tissue serving as the analysis target and on a basis of the information about the obstructive factor, generating assessment information used for assessing reliability of the perfusion images generated from the plurality of pieces of medical image data; and exercising control so that a predetermined display unit displays the assessment information.

* * * * *